Figure 1:
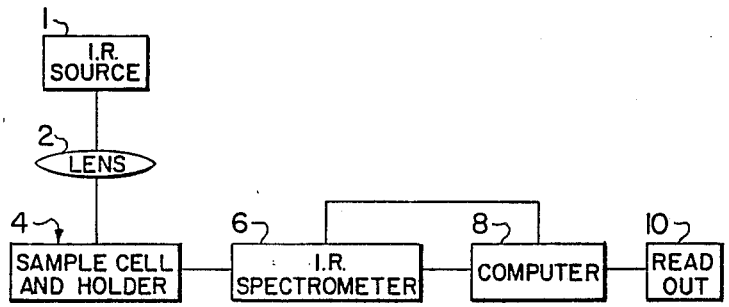

United States Patent [19]

Wong

[11] Patent Number: 4,970,396
[45] Date of Patent: Nov. 13, 1990

[54] INFRARED SPECTRA RECORDING, HIGH PRESSURE SAMPLE HOLDER

[75] Inventor: Patrick T. T. Wong, Ottawa, Canada

[73] Assignee: National Research Council of Canada/Conseil National de Recherches du Canada, Ottawa, Canada

[21] Appl. No.: 456,351

[22] Filed: Dec. 26, 1989

[51] Int. Cl.$^5$ ............................ G01J 5/04; G01J 5/06
[52] U.S. Cl. ................................ 250/338.1; 250/343; 356/440; 356/244
[58] Field of Search ............................ 250/338.1, 343; 356/440, 244

[56] References Cited

U.S. PATENT DOCUMENTS 3,509,597  5/1970  Kirk ................................ 356/244

FOREIGN PATENT DOCUMENTS 1410492  10/1975  United Kingdom ................ 356/244

OTHER PUBLICATIONS

Welber, *Optical Microspectroscopic System for Use With a Diamond Anvil High Pressure Cell to 200 Kilobar*, Rev. Sci. Instrum., vol. 47, No. 2, 2/76, pp. 183–186.
Clark et al., *A Tetrahedral Anvil Apparatus for Optical Studies Under High Hydrostatic Pressures*, J. Phys. E. (GB), vol. 6, No. 1, 1/73, pp. 43–47.

Primary Examiner—Constantine Hannaher
Assistant Examiner—Jacob M. Eisenberg
Attorney, Agent, or Firm—Francis W. Lemon

[57] ABSTRACT

An infrared absorption spectra recording, high pressure sample holder comprises a gasket for high compression between two diamond anvils, and an infrared light beam transmitting material partially filling a light passage through the gasket at a position between the two anvils to leave an infrared light beam transmitting, sample cavity adjacent one anvil. The surface of the filling is shaped, e.g. dished so that an infrared light beam passing through the sample will have light paths of different lengths, thereby avoiding optical interference fringes.

5 Claims, 4 Drawing Sheets

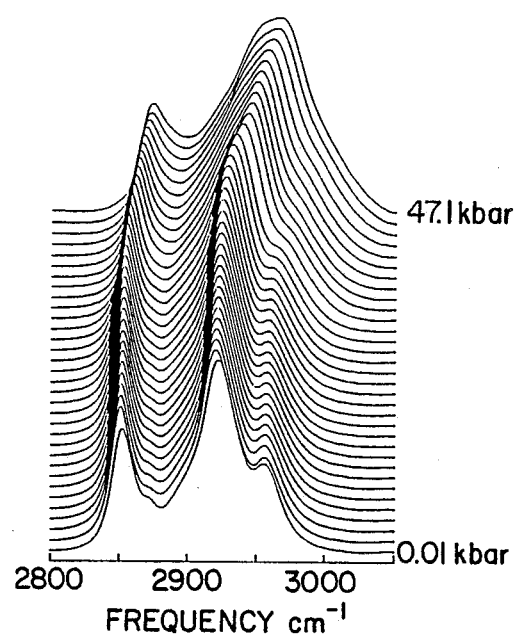
FIG. 8
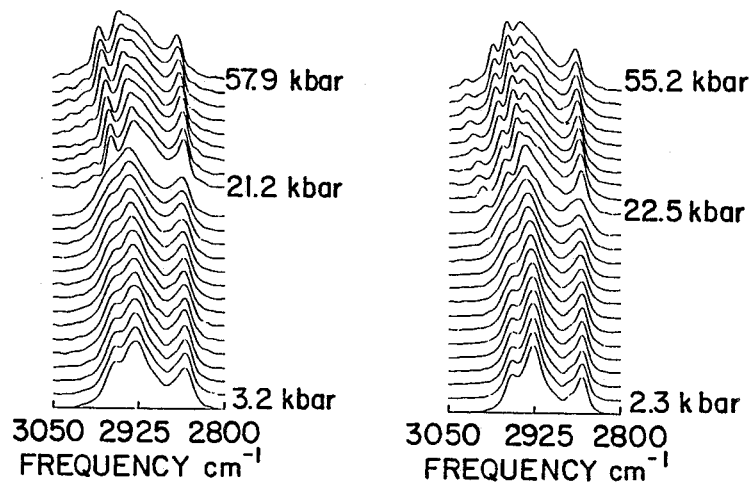
FIG. 9a
FIG. 9b

INFRARED SPECTRA RECORDING, HIGH PRESSURE SAMPLE HOLDER

This invention relates to a sample holder for recording infrared absorption spectra under high pressure.

The opposed anvils, high pressure, infrared absorption, spectra measuring technique, is generally described by the applicant in "Vibrational Spectra and Structure, A Series of Advances", "Opposed Anvil Cell", Chapter 6, pages 359–363, published by Elsevier, 1987. This technique comprises passing a condensed, infrared beam through, for example, calcium fluoride anvils between which a sample is compressed to a high pressure in a metal gasket forming a sample holder, so that structural and dynamic properties of the sample can be studied by analysis from the infrared absorption spectra of the pressure dependancies of the spectral parameters thereof.

While this opposed anvils, high pressure, infrared absorption spectroscopic technique is useful for samples having a high degree of transparency with respect to the infrared light beam, a problem has been found with other samples having relatively high infrared absorption in that a practical thickness of the sample holder, which would withstand the high pressure to which the sample is subjected, caused the sample to totally absorb the condensed light beam.

It has already been proposed by D.D. Klug and E. Whalley, see FIG. 2, page 1221 of the Journal of Chemical Physics, Volume 81, 1981, to provide a sample holder about 50 microns in thickness but interference fringes were found to be a problem to obtain a useful infrared absorption spectrum. The sample holder was also found to be difficult to manufacture and was liable to rupture when subjected to the high sample pressure needed.

There is a need for a high pressure, infrared absorption spectra sample holder in which samples of substances having a relatively high infrared absorption can be used without interference fringes being present, and wherein the sample holder is easily manufactured and capable of withstanding the high pressure in use.

According to the present invention there is provided an infrared absorption spectra recording, high pressure sample holder, comprising:
(a) a sample gasket of high compressive strength material which is substantially unreactive to a sample, the gasket having,
  (i) opposed, anvil engaging surfaces, and
  (ii) a condensed, infrared light beam transmitting passage extending between, and bounded by, the anvil engaging surfaces, and
(b) a filling in the passage, the filling being
  (i) unreactive to the sample,
  (ii) capable of transmitting an infrared light beam,
  (iii) partially filling the passage to leave a sample cavity at one end thereof, and
  (iv) shaped at the surface thereof bounding the sample cavity to provide adjacent, condensed, infrared light beam paths through the sample cavity which are different in length, whereby, in operation,
(c) with an infrared light beam transmitting sample compressed to high pressure in the cavity between opposed, infrared light transmitting anvils, which close the passage by contacting the anvil engaging surfaces, the passage of a condensed, infrared light beam through the sample, along the adjacent light paths of different lengths, will avoid introducing optical interference fringes in the infrared spectra, and the high quality infrared absorption spectra of the sample will be readily obtained.

The surface of the material bounding the sample cavity may be dish-shaped.

The filling may be a fine powder of at least one material selected from the group consisting of AgCl, TlI/TlBr, $BaF_2$, $CaF_2$, ZnTe, MgO. KBr, NaCl, LiF, KCl and ZnS.

The sample holder may contain a minor amount of an internal pressure calibrant in the sample cavity.

The internal pressure calibrant is preferably a substance from the group consisting of $\alpha$-quartz, $BaSO_4$ and HOD.

The present invention has made high pressure infrared absorption, spectra technique a new and useful approach to examine, for example, liquids, solids, aqueous systems and aqueous biological systems and lipids, proteins, nucleic acids (DNA and RNA), hydrocarbons, and animal or vegetable tissues (alive or dead) and bacteria. The applicant has demonstrated that, using the present invention, high pressure, infrared spectroscopy is a very powerful technique for monitoring the changes in the structure and dynamic properties of lipids as well as proteins in biological systems, and to analyze them in situ, without extracting them from the biological tissues and specimens. The molecular components in the tissues can be examined in their undisturbed environment in this way.

Figures 2, 3:
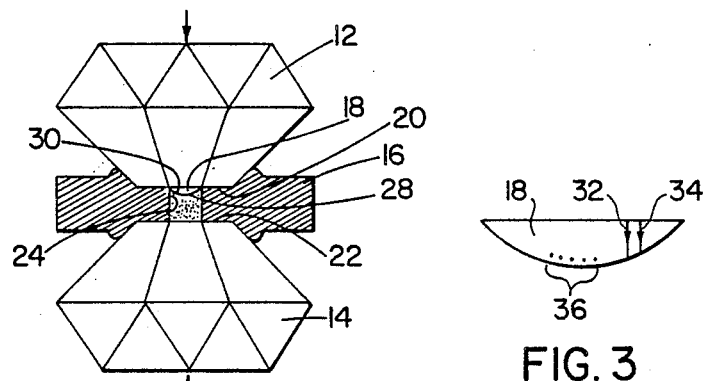
Figures 4, 5:
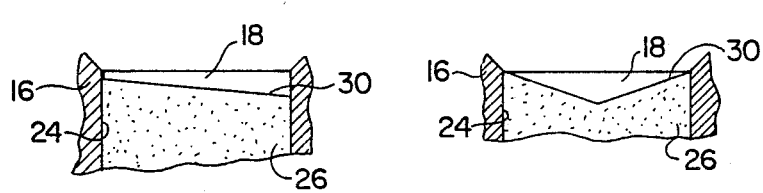
Figure 10:
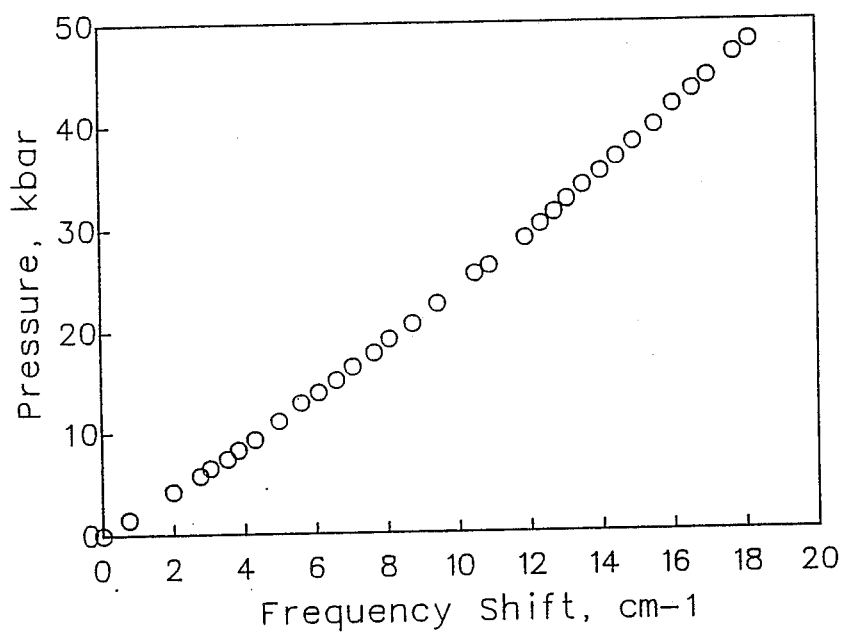

In the accompanying drawings which illustrate, by way of example, embodiments of the present invention, FIG. 1 is a block diagram of a high pressure, infrared absorption, spectroscopic apparatus, FIG. 2 is an enlarged, partly sectional side view of the hiqh pressure, infrared absorption, spectra, sample holder shown in FIG. 1, FIG. 3 is an even more enlarged side view of the sample shown in FIG. 2, FIGS. 4 and 5 are scrap, enlarged partly sectional side views showing different filling contours from those shown in FIG. 2, FIGS. 6 to 8, 9a and 9b show the stacked contour plots of the infrared absorption spectra at increasing pressure of different samples, and FIG. 10 shows the frequenCy shift of the symmetric $SO_4$=stretching mode of $BaSO_4$ with respect to pressure.

In FIG. 1 and 2, there is shown an infrared light beam source 1, a convex lens 2, a sample cell and assembly holder generally designated 4, an infrared spectrometer 6, a computer 8, and a read-out 10.

As shown in FIG. 2, the sample holder assembly 4 comprises two opposed diamond anvils 12 and 14, and an infrared absorption, spectra recording, high pressure sample holder, comprising:
(a) a sample gasket 16, shown in the deformed state, of high compressive strength material which is substantially unreactive to a sample 18, the gasket 16 having,
  (i) opposed, anvil engaging surfaces 20 and 22, and
  (ii) a condensed, infrared light beam transmitting passage 24 extending between, and bounded by, the anvil engaging surfaces 20 and 22, and
(b) a filling 26 in the passage 24, the filling 26 being
  (i) unreactive to the sample 18,
  (ii) capable of transmitting an infrared light beam, (iii) partially filling the passage 24 to leave a sample cavity 28 at one end thereof, and (iv) shaped, in the embodiment dished, at the surface 30 thereof bounding the sample cavity 28 to provide adjacent infrared light beam paths, such as light beam paths 32 and 34 in FIG. 3, which are different in length.

The infrared light beam source 1 may be any conventional infrared light beam source.

The convex lens 2 may be of NaCl or KBr, but may also be of $BaF_2$, $CaF_2$, AgCl, ZTe, MgO, KRS-5 ® or Irtran 1-6 ®.

The most common material for the anvils 12 and 14 is diamond due to its hardness. For infrared and for infrared measurements type II a diamond is commonly used. Calcium fluoride anvils have also been used with a working pressure up to 6 K bar.

Suitable materials for the gasket 16 are Inconel X 750 ®, T 301 Stainless Steel ®, and Waspalloy ®. While the thickness of the gasket 16 is not critical, thicknesses in the range of 0.1 to 0.25 mm have been found to be suitable.

The filling 26 is preferably a soft solid in powder form such as, for example, AgCl or TlI/TlBr. However, a hard solid in powder form such as, for example, $BaF_2$, $CaF_2$, ZnTe or MgO, may also be used, or mixtures thereof.

In operation, a sample 18 is placed in the cavity 28 and is compressed therein as shown in FIG. 2 by the anvils 12 and 14 in a conventional manner by means not shown.

An infrared light beam from the source 1 is condensed by the convex lens 2 and passed through the anvil 12, the sample 18, the filling 26, and the anvil 14.

With the sample 18 compressed to high pressure in the cavity 30 between the opposed, infrared light beam transmitting anvils 12 and 14, which close the passage 24 by contacting the anvil engaging surfaces 20 and 22, the passage of the condensed, infrared light beam from the convex lens 2 through the sample 18, along the adjacent light paths of different lengths, such as light paths 32 and 34, avoids optical interference fringes in the infrared spectra, and the infrared absorption spectra of the sample is readily recorded by the infrared spectrometer 6. These spectra obtained by the spectrometer are analyzed by the computer 8 which is programmed to deduce structural and dynamic behaviour at the molecular level of the material of the sample 18 under perturbation of high pressure. These data are fed from the computer 8 to the read-out 10.

The following are examples of tests made to verify the present invention using the apparatus described with reference to FIGS. 1-3.

Example I

The infrared absorption spectra were recorded at increasing pressure of rat liver tissues in the frequency region of 1300 to 1800 $cm^{-1}$.

Figure 6:
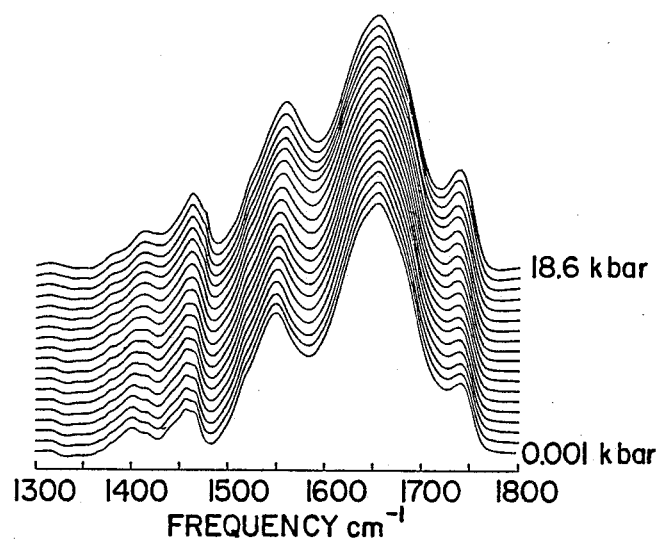

The results are shown in FIG. 6, which shows stacked contour plots of the infrared absorption spectra at increasing pressure (kbar) of rat liver tissue.

Example II

The infrared absorption spectra were recorded at increasing pressure of liquid (<1.4 kbar) and solid (>1.4 kbar) of n-pentadecane in the frequency region of 1420 to 1500 $cm^{-1}$.

Figure 7:
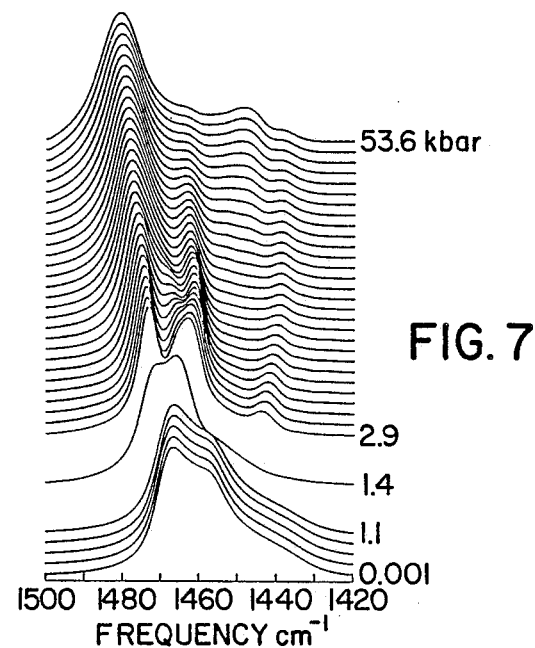

The results are shown in FIG. 7 which shows stacked contour plots of the type shown in FIG. 6.

Example III

The infrared absorption spectra were recorded at increasing pressure of aqueous dispersions of DMPC lipid in the frequency region of 2800 to 3050 $cm^{-1}$.

The results are shown in FIG. 8 which shows stacked contour plots of the type shown in FIG. 6.

Example IV

The infrared absorption spectra were recorded at increasing pressure of aqueous micellar solutions of sodium and potassium decanoates in the frequency region of 2800 to 3050 $cm^{-1}$.

The results are shown in FIG. 9a for sodium decanoate and FIG. 9b for potassium decanoate, both of which show stacked contour plots of the type shown in FIG. 6.

While the surface 30 of the filling 26 may be shaped to any contour that will provide the sample 18 with adjacent light beam paths which are of different lengths, it is preferable that the surface 30 be of a contour that can easily be produced by, for example, the end of a rod.

In FIGS. 4 and 5, similar parts to those shown in FIGS. 2 and 3 are designated by the same reference numerals and the previous description is relied upon to describe them.

In FIG. 4, the surface 30 is shown inclined from one side of the passage 24 to the other side thereof.

In FIG. 5, the surface 30 is shown cone-shaped.

In other embodiments of the present invention, a few particles, designated 36 in FIG. 3, of an internal pressure calibrant are included in the sample caviity.

Suitable internal pressure calibrants are, for example, α-quartz, $BaSO_4$ and HOD.

An example of tests to verify these embodiments of the present invention is given in FIG. 10 wherein the frequency shift ($cm^{-1}$) of the symmetric $SO_4$=stretching mode of $BaSO_4$ is plotted with respect to pressure (kbar).

These tests showed that the minor amount of an internal pressure calibrant in the sample cavity had no noticeable effect on the quality of the infrared absorption spectra recorded.

I claim:

1. An infrared absorption spectra recording, high pressure sample holder, comprising:
   (a) a sample gasket of high compressive strength material which is substantially unreactive to a sample, the gasket having,
      (i) opposed, anvil engaging surfaces, and
      (ii) a condensed, infrared light beam transmitting passage extending between, and bounded by, the anvil engaging surfaces, and
   (b) a filling in the passage, the filling being
      (i) unreactive to the sample,
      (ii) capable of transmitting an infrared light beam,
      (iii) partially filling the passage to leave a sample cavity at one end thereof, and
      (iv) shaped at the surface thereof bounding the sample cavity to provide adjacent, infrared light beam paths through the sample cavity which are different in length, whereby, in operation,
   (c) with a sample compressed to high pressure in the cavity between opposed, infrared light beam transmitting anvils, which close the passage by contacting the anvil engaging surfaces, the passage of a condensed, infrared light beam through the sample, along the adjacent light paths of different lengths, will avoid introducing optical interference fringes in the infrared spectra, and the high quality infrared absorption spectra of the sample will be readily obtained.

2. A sample holder according to claim 1, wherein the surface of the filling bounding the sample cavity is dish-shaped.

3. A sample holder according to claim 1, wherein the filing is a powder of at least one material selected from the group consisting of AgCl, TlI/TlBr, $BaF_2$, $CaF_2$, ZnTe, MgO, KBr, NaCl, KCl, LiF, and ZnS.

4. A sample holder according to claim 1, further comprising a minor amount of an internal pressure calibrant in the sample cavity.

5. A sample holder according to claim 4, wherein the internal pressure calibrant is a substance selected from the group consisting of α-quartz, $BaSO_4$ and HOD.

* * * * *